United States Patent [19]

Banquy

[11] Patent Number: 4,546,111

[45] Date of Patent: Oct. 8, 1985

[54] PROCESS FOR THE PRODUCTION OF OXYGENATED ORGANIC COMPOUNDS SUCH AS METHANOL

[75] Inventor: David L. Banquy, Paris, France

[73] Assignee: Foster Wheeler Energy Corporation, Livingston, N.J.

[21] Appl. No.: 487,655

[22] Filed: Apr. 22, 1983

[51] Int. Cl.$^4$ ............................................. C07C 27/06
[52] U.S. Cl. ................................................... 518/703
[58] Field of Search ......................................... 518/703

[56] References Cited

U.S. PATENT DOCUMENTS

| | | | |
|---|---|---|---|
| 3,920,717 | 11/1975 | Marion | 518/703 |
| 4,218,389 | 8/1980 | Jackson et al. | 518/703 |
| 4,348,486 | 9/1982 | Calvin et al. | 518/704 |

FOREIGN PATENT DOCUMENTS

| | | | |
|---|---|---|---|
| 2445884 | 4/1976 | Fed. Rep. of Germany | 518/703 |
| 836909 | 6/1960 | United Kingdom | 518/703 |
| 1262479 | 2/1972 | United Kingdom | 518/704 |

*Primary Examiner*—Howard T. Mars
*Attorney, Agent, or Firm*—Marvin A. Naigur; John E. Wilson; Robert D. Bajefsky

[57] ABSTRACT

A process for the production of an oxygenated organic product, such as methanol, from a feedstock containing carbon, comprising the steps of: (a) gasifying the feedstock with high purity oxygen to obtain a raw synthesis gas stream comprising methane, hydrogen, and carbon oxides; (b) mixing the raw synthesis gas stream with a hydrogen-rich gas stream to form a final synthesis gas stream; (c) injecting the final synthesis gas stream into a synthesis loop, forming the oxygenated organic product in the loop and extracting from the loop a purge gas stream; (d) separating the purge gas cryogenically to form the hydrogen-rich gas stream, an argon-rich gas stream, and a methane-rich gas stream; and (e) recycling the hydrogen-rich gas stream to step (b).

24 Claims, 10 Drawing Figures

PROCESS FOR THE PRODUCTION OF OXYGENATED ORGANIC COMPOUNDS SUCH AS METHANOL

BACKGROUND OF THE INVENTION

This invention relates to processes for the production of methanol and other oxygenated hydrocarbons from feedstocks containing carbon. More specifically, the invention relates to the production of these compounds from a synthesis gas produced by the gasification with oxygen of such carbon containing feedstocks.

Methanol may be industrially synthesized from a synthesis gas containing hydrogen, carbon monoxide, and carbon dioxide, along with small amounts of inert gases such as methane, argon, and nitrogen. The conversion follows one of two reactions:

$$2H_2 + CO \rightarrow CH_3OH$$

$$3H_2 + CO_2 \rightarrow CH_3OH + H_2O$$

Methanol synthesis gas may be produced by any one of several known industrial processes, such as catalytic steam reforming, as exemplified by the process described in U.S. Pat. No. 2,829,113; catalytic oxygen reforming, such as, for example, the process described in French Pat. No. 1,158,617; and partial oxidation, such as, for example, the process described in U.S. Pat. No. 3,962,300.

When the feedstock is a light hydrocarbon such as natural gas, it is usually subjected to steam reforming to produce the synthesis gas required for methanol, and the reformed gas has a large excess of hydrogen above the stoichiometric requirement for the synthesis gas. When the feedstock is a heavy hydrocarbon such as a fuel oil, the most common method in use for producing the synthesis gas is the partial oxidation process, such as described in U.S. Pat. No. 3,962,300. Such a partial oxidation process produces a raw synthesis gas containing CO and $CO_2$ in excess of stoichiometric requirements. Accordingly, some amount of carbon oxides (usually only $CO_2$) must be removed from the system to correct for this excess. In the conventional processes, the most common correction method is to subject at least part of the gas produced by gasification to a shift conversion reaction, and then remove $CO_2$ and $H_2S$ from the gas to obtain a purified synthesis gas having the stoichiometric composition, and a very low methane content of less than about 0.6 mole percent.

When the feedstock is coal, the processing schemes that have been proposed or used are similar to that for fuel oil described above. The coal is gasified with oxygen in an adiabatic reactor, at a temperature above 1,400° C., giving a raw synthesis gas with a methane content of less than about 0.6 mole percent.

A disadvantage of conventional schemes for producing synthesis gas for the production of methanol and other oxygenated organic compounds from fuel oil or coal feedstocks is that a very large amount of oxygen is necessary to obtain the high temperature (in the range of 1,300° C. to 1,600° C.) required, and to achieve the required methane content of less than about 0.6 mole percent on a dry basis in the effluent gas from the gasifier. A second disadvantage is that the purge gas from the synthesis reactor, which must be removed from the gases recycled to the synthesis reaction to prevent hydrocarbons and other inerts from reaching unacceptable levels in the reactor, includes some unreacted $H_2$ and CO. The removal of these potential reactants reduces the overall efficiency of the process. In addition, the shift conversion reaction that is performed on the raw synthesis gas is an expensive operation due to the high CO concentration in the gas produced by gasification of the feedstock.

SUMMARY OF THE INVENTION

An object of the present invention is to reduce the overall energy requirement in the production of methanol and other oxygenated organic products by appreciably reducing the high purity oxygen requirement in the gasification reactor, and by recovering and recycling to the process the hydrogen and carbon monoxide contained in the purge gas of the synthesis loop.

Another object of this invention is to reduce the capital cost of an oxygenated organic product plant using a heavy feedstock such as coal or oil.

Still another object of this invention is to make profitable use of any hydrocarbon contained in the purge gas of the oxygenated organic product reactor, by (1) recycling it to the gasification reactor and, when a solid feedstock is involved, using it as transport gas for the feedstock, or (2) reforming it to produce synthesis gas and utilizing the reformed gas in the synthesis process.

An additional object of this invention is to reduce, or even eliminate entirely, the need for shift converting part of the raw synthesis gas by removing $CO_2$ from the purge gas.

Additional objects and advantages of the invention will be set forth in part in the description that follows, and in part will be obvious from this description, or may be learned by practice of the invention. The objects and advantages of the invention may be realized and attained by means of the instrumentalities and combinations particularly pointed out in the appended claims.

To achieve the foregoing objects and in accordance with the purpose of the invention, as embodied and broadly described herein, the invention comprises a process for the production of an oxygenated organic product, such as methanol, from a feedstock containing carbon, comprising the steps of:

(a) gasifying the feedstock by reacting it with high purity oxygen to obtain a raw synthesis gas stream comprising methane, hydrogen, and carbon oxides;

(b) mixing the raw synthesis gas stream with a hydrogen-rich gas stream to form a final synthesis gas stream;

(c) injecting the final synthesis gas into a synthesis loop, forming the oxygenated organic product in said loop, and extracting from said loop a purge gas stream;

(d) separating the purge gas stream cryogenically to form a hydrogen-rich gas stream, an argon-rich gas stream, and a methane-rich gas stream; and (e) recycling the hydrogen-rich gas stream to step (b).

The invention further comprises the step of recycling at least part of the methane-rich stream by mixing it with the feedstock, or converting the methane-rich stream to a synthesis gas and mixing it with the hydrogen-rich gas stream and/or the raw synthesis gas stream which are supplied to the synthesis reactor.

DESCRIPTION OF THE PREFERRED EMBODIMENTS

Reference will now be made to the presently preferred embodiments of the invention as those embodiments relate to the production of methanol. The invention, however, may be used to produce any oxygenated organic product such as, for example, alcohols, ethers, ketones, glycols, or mixtures thereof.

The advantages of this invention over conventional schemes are derived from the features described below, and will be apparent to one skilled in the art.

Since, according to the present invention, the gasification reactor may operate at lower temperatures than conventional processes, less oxygen per ton of product produced is required. This provides an important energy saving in the process. As a consequence of using less oxygen in the gasification step, the invention also provides an investment saving per ton of product produced because the process may be used in a single train plant on a much larger scale. Moreover, since essentially all the $H_2$ and CO contained in the purge gas from the product synthesis step may be reused in the process, the feedstock consumption per ton of product produced is lower.

In addition, a great part, if not all, of the $CO_2$ may be removed from the purge gas, and thereby from the system, at high pressure prior to the cryogenic separation. Removal at this point in the process requires less energy and less capital investment than $CO_2$ removal carried out at the appreciably lower pressure of the gasification reactor.

Furthermore, in accordance with this invention, shift conversion is applied to the purge gas rather than the raw synthesis gas. Performing the conversion on the purge gas requires a smaller reactor because, in the synthesis reactor, some $CO_2$ is reacted with hydrogen and some is converted. Thus the amount of $CO_2$ which must be subjected to shift conversion is less in the purge gas than in the synthesis gas.

As noted above, the present invention permits the use of a lower temperature gasification reactor and, thus, requires less oxygen. This is a significant advantage because the presence of nitrogen and argon in air has necessitated the use of high purity oxygen rather than air in the gasification reactor. Usually above 98 mole percent pure oxygen is required to produce synthesis gas for methanol production. The use of less oxygen and the lower temperature, however, results in a synthesis gas having a high methane content. For example, the gas may contain from 1 to 10 mole percent methane on a dry basis. The present invention permits the use of such high methane containing synthesis gas.

Furthermore, the refrigeration requirements of the cryogenic separation may be at least partially supplied by expansion of the methane-rich stream and the argon-rich stream. The high methane content of the raw synthesis gas may, therefore, actually be beneficial.

The presently preferred embodiments of the invention are shown by the attached drawings. The purpose of the drawings is to illustrate some embodiments of the present invention without implying a limitation on the scope of the invention.

The invention comprises a process for the production of an oxygenated organic product from a feedstock containing carbon. As embodied herein, the feedstock may be composed essentially of hydrocarbons (gas, liquid, or solid), coal, shale oil, wood, organic compounds, or any combination thereof.

To accomplish the production of an oxygenated product, the invention comprises the step of gasifying the feedstock with high purity oxygen. As embodied herein, the gasification step comprises any known process available for partial oxidation of carbonaceous compounds, coal gasification, or catalytic oxygen reforming. When methanol is being produced, the gasification step should produce a raw synthesis gas containing at least one mole percent, preferably 1 to 10 mole percent, and more preferably 2 to 6 mole percent, methane. The process can also be used with synthesis gases containing less than one percent methane. However, since higher temperatures are required to produce such gases, many of the advantages of this invention will not be obtained using synthesis gases having less than one percent methane.

The operating pressure of the gasification reactor is preferably maintained above about 20 atm, and may be maintained as high as 100 atm. The operating temperature may be between about 800° C. and about 1,250° C. In a catalytic oxygen reforming process, the temperature is typically in the range of about 800° C. to about 1,000° C. In a partial oxidation process for residual oils, coal, or other solid feedstocks, a preferred gasification reactor operates as a fluid bed of particles at a temperature from about 950° C. to about 1,100° C.

The "U-Gas" process is an example of a gasification step which can be used with this invention. This process is described in an article entitled "The U-Gas Process," 71 *Chem. Eng. Progress* 85 (April, 1975).

Figure 1:
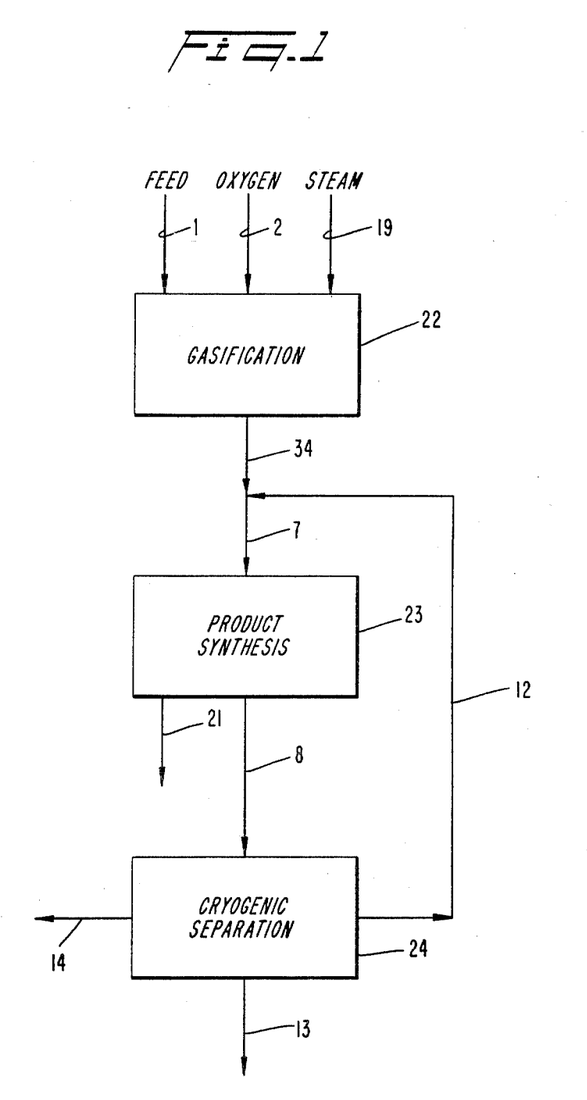
FIG. 1 is a block diagram of an embodiment of the process of the present invention showing the recycling of a hydrogen-rich stream to the synthesis reactor.

The gasification step is shown in FIG. 1, wherein a feedstock 1 containing carbon is combined with a high-purity oxygen stream 2 in a gasification apparatus 22. Steam stream 19 is also added to the gasification apparatus 22. A raw synthesis gas stream 34 is the effluent stream from apparatus 22.

The oxygen-rich gas stream 2 used for gasification is usually produced by air separation, and should have a purity of at least 95 mole percent oxygen and preferably at least 99 mole percent oxygen. It is common to use an oxygen stream containing 99.5 percent oxygen by air separation. The steam added through line 19 is usually added in a ratio of 0.2–1.0:1.0 by weight to the feedstock.

Figure 8B:
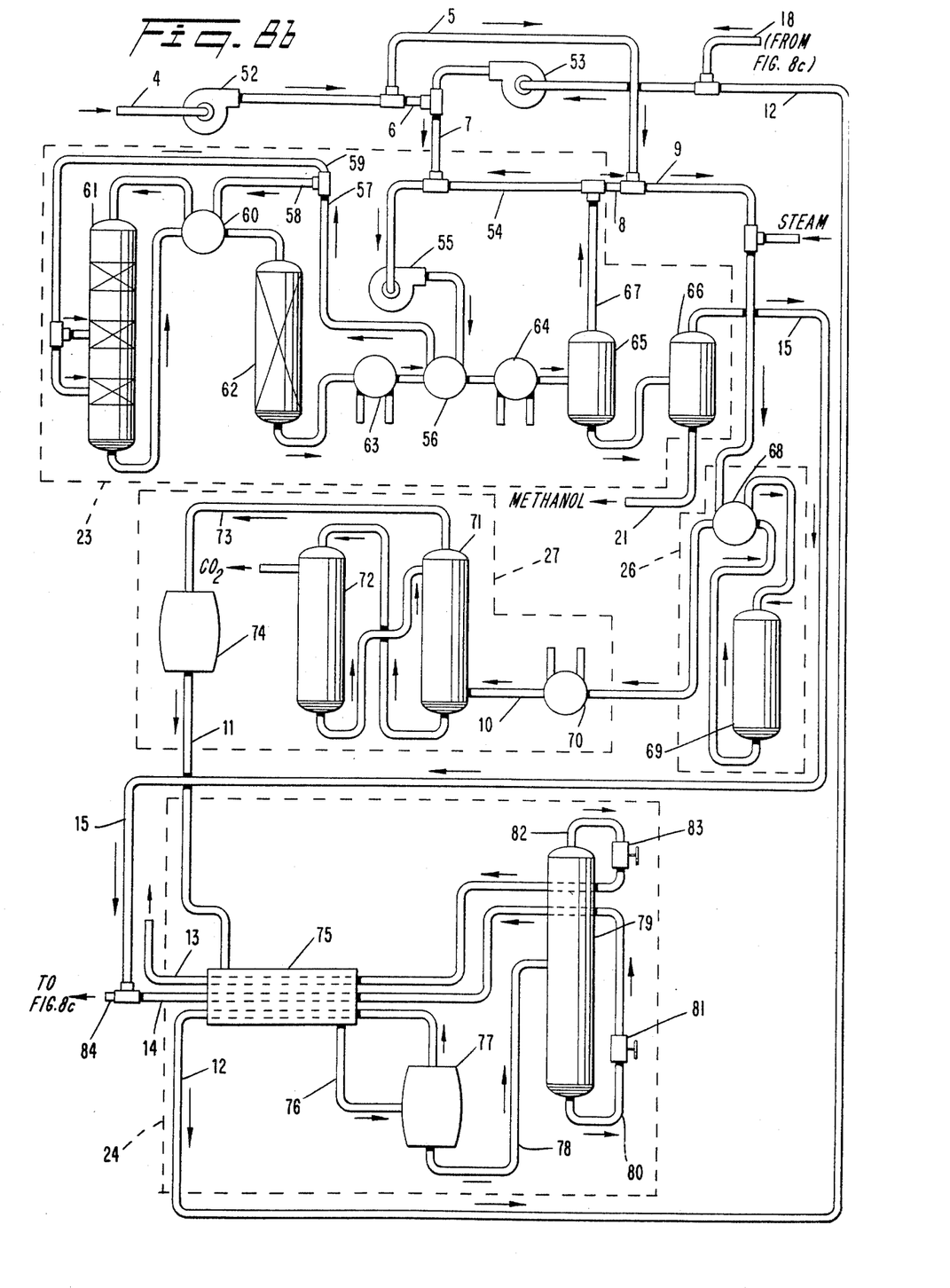
FIG. 8, which is comprised of FIGS. 8A, 8B and 8C, is a schematic drawing of a preferred embodiment of the invention.

If the raw synthesis gas stream 34 contains ash from the reactor, the ash may be separated in a cyclone separator as shown in FIG. 8B or by other conventional means.

The invention comprises the step of mixing a recycle hydrogen-rich stream with the raw synthesis gas stream to form a final synthesis gas stream. As shown in FIG. 1, raw synthesis gas stream 34 is joined with a recycle hydrogen-rich stream 12 to form a final synthesis gas stream 7.

The invention comprises the step of forming an oxygenated product, such as methanol, from the final synthesis gas stream. As embodied herein and illustrated by FIG. 1, the formation step takes place in a product synthesis loop 23. A crude product stream 21 and a purge gas stream 8 are removed from the product synthesis loop 23. The amount of purge gas removed should be sufficient to maintain the amount of methane circulating in the synthesis loop between about 5 and about 35 mole percent, preferably between about 10 and about 20 mole percent. Any known process for the synthesis of methanol or other oxygenated hydrocarbon can be used. The particular synthesis process selected is not part of this invention.

The process of the invention comprises the further step of separating the purge gas cryogenically to form a hydrogen-rich stream, an argon-rich stream, and a methane-rich stream. In FIG. 1, the cryogenic separation unit 24 produces three streams: hydrogen-rich stream 12, argon-rich stream 13, and methane-rich stream 14. The argon-rich stream 13 from cryogenic separation unit 24 may be used for heat exchange for cryogenic purposes, and, since it contains a significant amount of methane, for fuel.

As embodied herein in the synthesis of methanol, the cryogenic separation unit 24 comprises a fixed cryogenic heat exchanger and a cryogenic distillation column arranged in series. The purge gas stream 11 introduced into the cryogenic exchanger should preferably contain no more than about one ppm by volume of $CO_2$ and $H_2O$.

A liquid stream and a gas stream are produced in the cryogenic heat exchanger. In a preferred embodiment of the cryogenic separation unit, the gas stream leaving the exchanger is the hydrogen-rich stream 12 and contains an appreciable part of the CO that was in purge gas stream 11. The liquid contains essentially all the methane and most of the argon from purge gas stream 11. The liquid stream is sent to the cryogenic distillation column which is designed to separate this stream into an argon-rich stream and a methane-rich stream.

Some hydrogen is in argon-rich stream 13 and in methane-rich stream 14. However, the amount is small, generally less than 6 percent of the total hydrogen contained in the purge gas stream 11. The amount of argon contained in the hydrogen-rich stream is generally less than 15 percent of the total argon and preferably about 10 percent. The degree of separation between argon and methane in the cryogenic distillation column does not need to be very high, because only the argon introduced with the high purity oxygen in the feedstock gasification step must be removed. The carbon monoxide contained in the purge gas will be split between the argon-rich stream and the hydrogen-rich stream, with the fraction in the hydrogen-rich stream being about 30 to 70 percent of the total CO present in purge gas stream 11. It is usually preferable, therefore, to subject purge gas stream 11 to a shift conversion reaction, even if, as will be discussed below, the raw synthesis gas 34 has also been shift converted.

The argon-rich stream 13 is preferably used as fuel. The hydrogen-rich stream 12 is recycled to the product synthesis loop 23, as shown in FIG. 1, by mixing with raw synthesis gas stream 34.

In the discussion that follows, other embodiments of the invention will be described. Each embodiment will exemplify some advantages of the invention by focusing on one aspect of the invention, and the various embodiments may be combined to form embodiments not explicitly discussed, but still within the scope of the invention.

Figure 2:
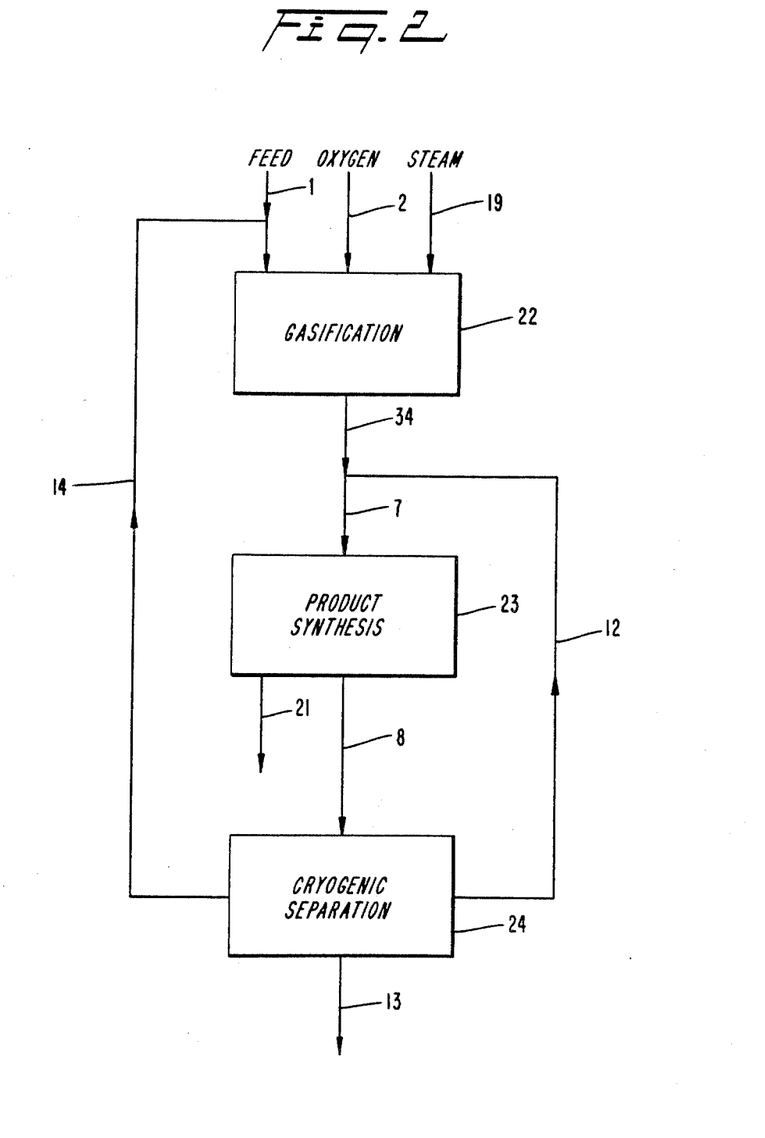
FIG. 2 is a block diagram showing an embodiment of the invention in which the methane-rich stream is recycled to the gasification reactor.

The invention may also comprise the step of recycling at least part of the methane-rich stream by mixing with the feedstock. As embodied herein and as shown in FIG. 2, the methane-rich stream 14 is recycled from the cryogenic separation unit 24 to the original feed stream 1. Methane-rich stream 14 may also be fed directly to gasification reactor 22. In either case, the methane-rich stream may be used to fluidize the feedstock 1, if appropriate.

Figure 3:
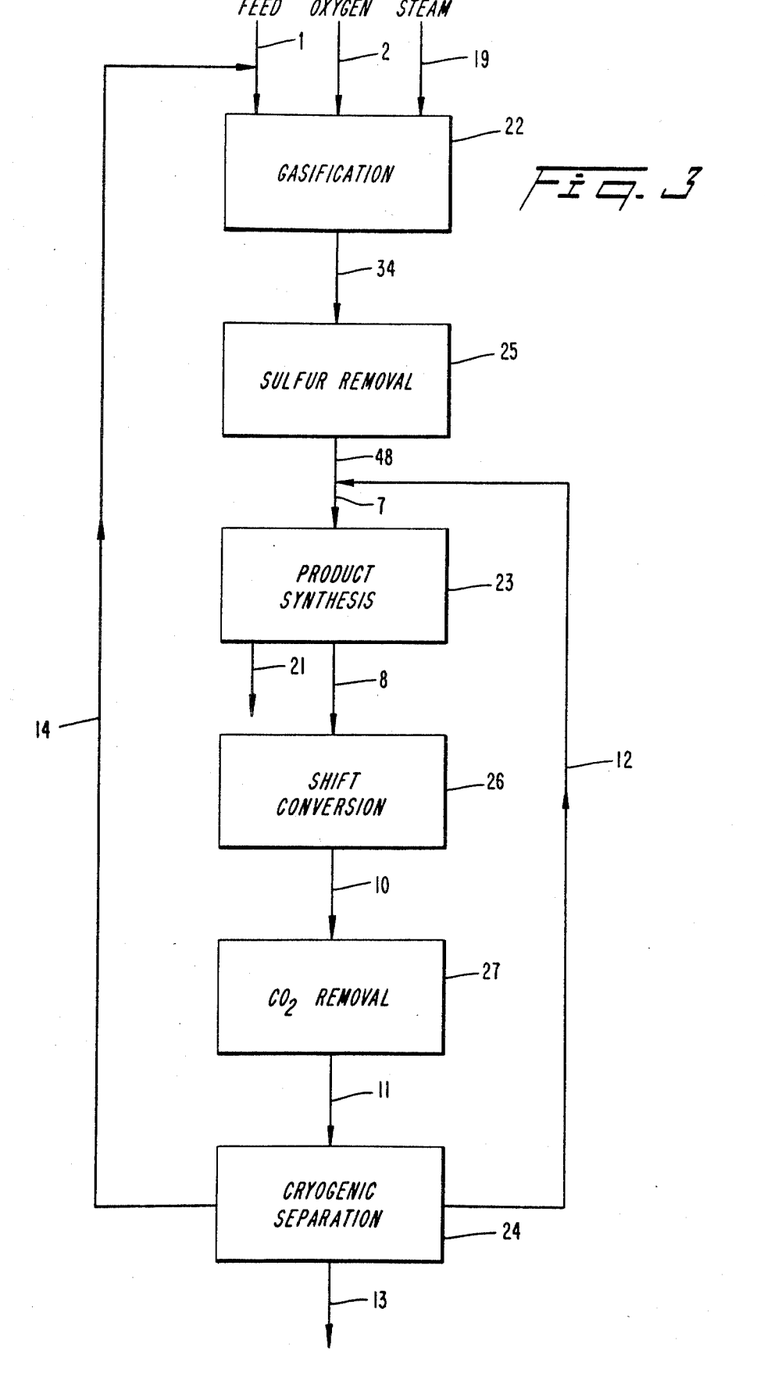
FIG. 3 is a block diagram showing another embodiment of the invention showing additional steps that may be used for treating the purge gas from the synthesis reactor and the raw synthesis gas stream.

In FIG. 3 the step of removing sulfur containing compounds from raw synthesis gas stream 34 is shown. Any means for removing sulfur compounds known in the art can be used. In FIG. 3 and elsewhere the step of sulfur removal is shown as block 25. Sulfur removal by solvent extraction is preferred in the present invention. Preferred solvents include methanol, dimethyl ether of polyethyleneglycol, and N-methyl-2 Pyrrolidone. The use of these solvents is well known in the art.

A sulfur removal step is usually necessary in the synthesis of methanol since sulfur is a strong poison to methanol synthesis catalysts currently in use. Therefore, essentially all the sulfur compounds must be removed from a synthesis gas feeding a methanol synthesis apparatus. Less than 1 ppm by volume sulfur is generally required for methanol synthesis and preferably less than 0.2 ppm by volume. If a catalyst that is insensitive to sulfur is used in the synthesis loop, or if a feedstock without sulfur-containing compounds is used, the sulfur removal step may not be necessary.

FIG. 3 also illustrates subjecting the purge gas stream 8, leaving product synthesis 22, to shift conversion and $CO_2$ removal before cryogenic separation. Any known processes for performing these steps can be used. While these steps are not essential, they provide certain operating advantages. By way of example, if $CO_2$ is not removed from the purge gas, solid $CO_2$ will accumulate in the cyogenic heat exchanger. Another cryogenic exchanger will then have to be provided so that one exchanger may be derimed to remove $CO_2$ deposits by vaporization while the other exchanger is in operation. A similar problem will occur if the purge gas is not dried before cryogenic separation. In that case, ice may form in the cryogenic exchanger.

Scrubbing in a tower with an appropriate solvent is a preferred method for removing $CO_2$ from purge gas stream 8. The solvent is regenerated in a second tower. The towers may be equipped with gas-liquid contact devices such as trays or packings. Any known process for $CO_2$ removal is acceptable in the process of the invention.

Shift conversion comprises reacting the purge gas stream 8 with steam in the presence of a shift catalyst to convert essentially all carbon monoxide in the purge stream to carbon dioxide and hydrogen. The shift catalyst that is preferred in this process may be either a "high temperature" shift (HTS) catalyst, based on iron and chromium oxides, or a "low temperature" shift (LTS) catalyst which is based on copper and zinc oxides. An HTS catalyst operates usually at a temperature between 380° C. and 480° C., whereas the LTS catalyst operates at a temperature between 180° C. and 260° C.

Figure 4:
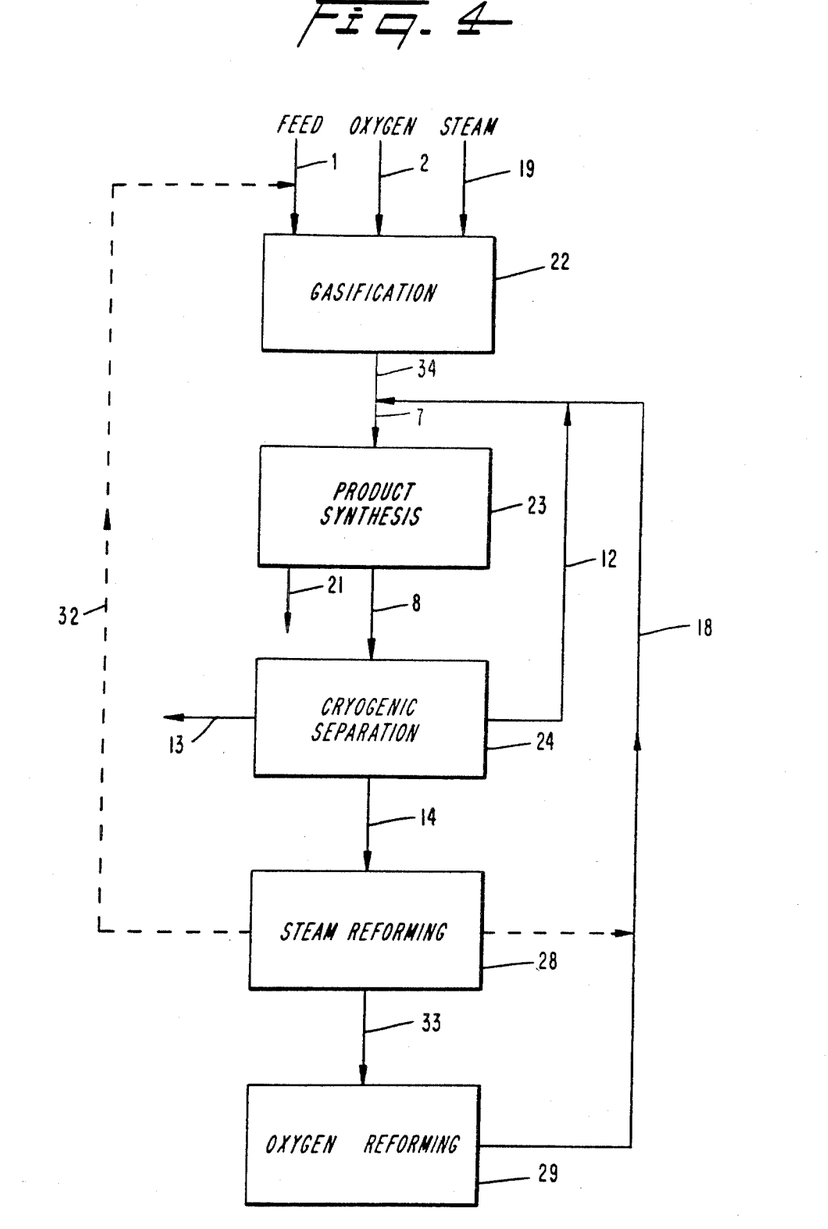
FIG. 4 is a block diagram of an embodiment of the invention wherein the methane-rich stream is subjected to stream reforming and then combined with the synthesis gas.

FIG. 4 illustrates an alternative method of recycling the methane-rich stream. In this embodiment of the invention the methane-rich stream 14 is subjected to a steam reforming step and, an optional subsequent oxygen reforming step. The reformed gas is recycled to the synthesis step or the gasification step. As embodied herein, the steam reforming step comprises introducing the methane-rich stream 14 and steam into a steam reformer 28. The reformer 28 contains tubes filled with reforming catalyst and is maintained at a temperature between about 600° C. and about 1,000° C. The effluent of the steam reformer may be recycled to the gasification step as stream 32. Alternately, all or part of the methane-rich stream 14 can be converted to synthesis gas by steam reforming followed, where appropriate, by oxygen reforming.

The steam reforming step 28 of FIG. 4, methane-rich stream 14 is preheated to a temperature between 200° C. and 400° C. and combined with steam. The mixture is further preheated to a temperature between 350° C. and 650° C., and is injected into a series of heated catalyst tubes contained in a steam reformer. The catalyst used in these tubes is a conventional catalyst essentially comprising nickel over a refractory support. The catalyst tubes are heated by a set of burners in appropriate locations.

If only steam reforming is to be used, the outlet temperature from the reforming tubes should be between 800° C. and 1,000° C., and the residual methane content of the synthesis gas stream leaving the catalyst tubes should be about 1 to 8 mole percent on a dry basis. The synthesis gas may be cooled, recycled as stream 18, and mixed with the raw synthesis gas stream 34.

If steam reforming is to be followed by oxygen reforming, the outlet temperature of the steam reforming apparatus 28 should be between 650° C. and 850° C., and the residual methane content of the gas leaving the catalyst tubes should be between about 10 and 50 mole percent on a dry basis. This gas stream is introduced into oxygen reformer 29 through line 33.

As embodied herein, the oxygen reforming step comprises reacting the effluent from the steam reforming step 28 with an oxygen-rich gas stream in an adiabatic reactor over a reforming catalyst. The oxygen stream is preferably preheated to a temperature from about 300° C. to about 550° C. An appropriate reforming catalyst is usually made of nickel on a refractory support. The operating temperature in the oxygen reformer is usually between 880° C. and 1,150° C., and is preferably between 940° C. and 1,050° C. The residual methane content of the effluent from the oxygen reformer is generally in the range of 0.5 to 5 mole percent on a dry basis, and preferably in the range of 1.5 to 3.0 mole percent. The oxygen stream normally comes from the same source as oxygen stream 2 and usually has the same purity. The effluent from the oxygen reforming step is recycled via stream 18 and combined with synthesis gas 34.

Figure 5:
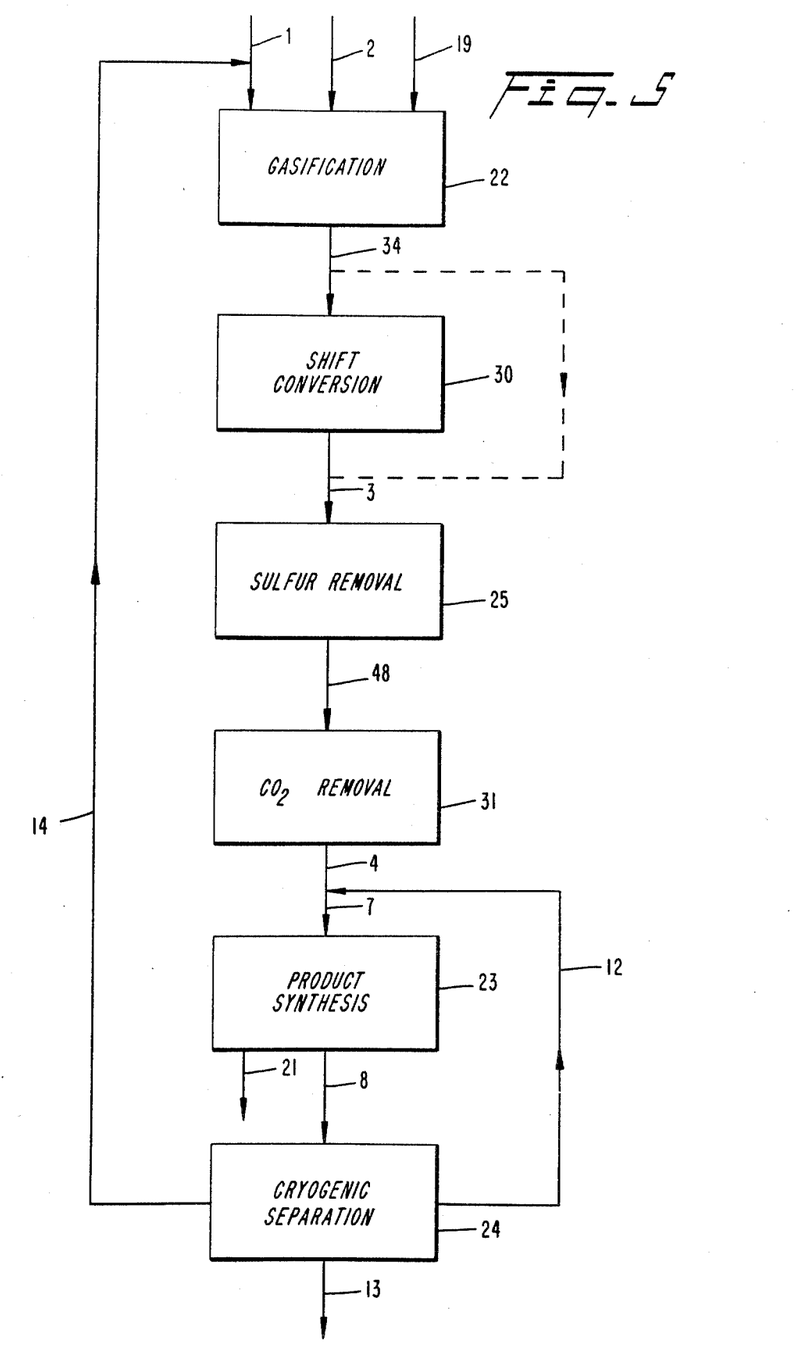
FIG. 5 is a block diagram showing steps that may be used for the treatment of the raw synthesis gas.

FIG. 5 shows an embodiment of the invention in which the raw synthesis gas is subjected to the steps of shift conversion, sulfur removal, and $CO_2$ removal. In this embodiment raw synthesis gas stream 34 is introduced into shift conversion apparatus 30. If only a portion of the raw synthesis gas is to be subjected to shift conversion, the remaining gas will bypass the converter as shown by the dotted line in FIG. 5.

Shift conversion 30 is carried out before sulfur removal 25 in FIG. 5. The low temperature shift catalyst that may be used in the shift conversion step 26 shown in FIG. 3 is sensitive to sulfur and may not be used in the present shift conversion step. The high temperature shift catalyst discussed above, however, may be used. In addition, a "medium temperature" shift (MTS) catalyst may be used. The MTS catalyst is based on cobalt and molybdenum as active components and is active in the presence of sulfur compounds. The MTS catalyst operates in a temperature range between 300° and 400° C. The converted synthesis gas stream 3 is then introduced into sulfur removal apparatus 25. The effluent from the sulfur removal step can then be supplied directly to the synthesis reactor. Alternatively, all or a portion of the effluent stream 48 from the sulfur removal step 25 can be transported to $CO_2$ removal apparatus 31. The synthesis gas stream 26 leaving the $CO_2$ removal step 31 is then combined with the recycled hydrogen-rich stream 12 and supplied to the synthesis loop.

If the raw synthesis gas is at least partially shift converted, then it is usually necessary to remove $CO_2$ before injecting the synthesis gas into the synthesis loop because the amount of $CO_2$ in the final synthesis gas that can be tolerated by most methanol synthesis processes is in the range of 2 to 10 mole percent on a dry basis, and most preferably in the range of 3 to 7 mole percent. Recycling of the hydrogen-rich stream and the methane-rich stream reduces the amount of $CO_2$ that needs to be removed.

In FIG. 5 the shift conversion step occurs before the sulfur removal step. The shift conversion step, however, could also be located downstream of the desulfurization step. If sulfur removal is performed before shift conversion, a conventional low temperature shift catalyst, operating in a temperature range from about 200° to 230° C., can be used. This catalyst would result in a low residual CO content in the effluent from the shift conversion reactor, in the order of 0.3 to 0.6 volume precent on a dry basis. Sulfur removal before shift conversion, however, complicates the process and requires more overall energy because of the cooling-heating cycle that would be performed on the synthesis gas if this sequence of operating steps were followed. It is advantageous, however, for shift conversion to occur before sulfur removal because the shift reaction converts COS, a sulfur compound formed during gasification, to $H_2S$ which is easier to remove than COS.

Figure 6:
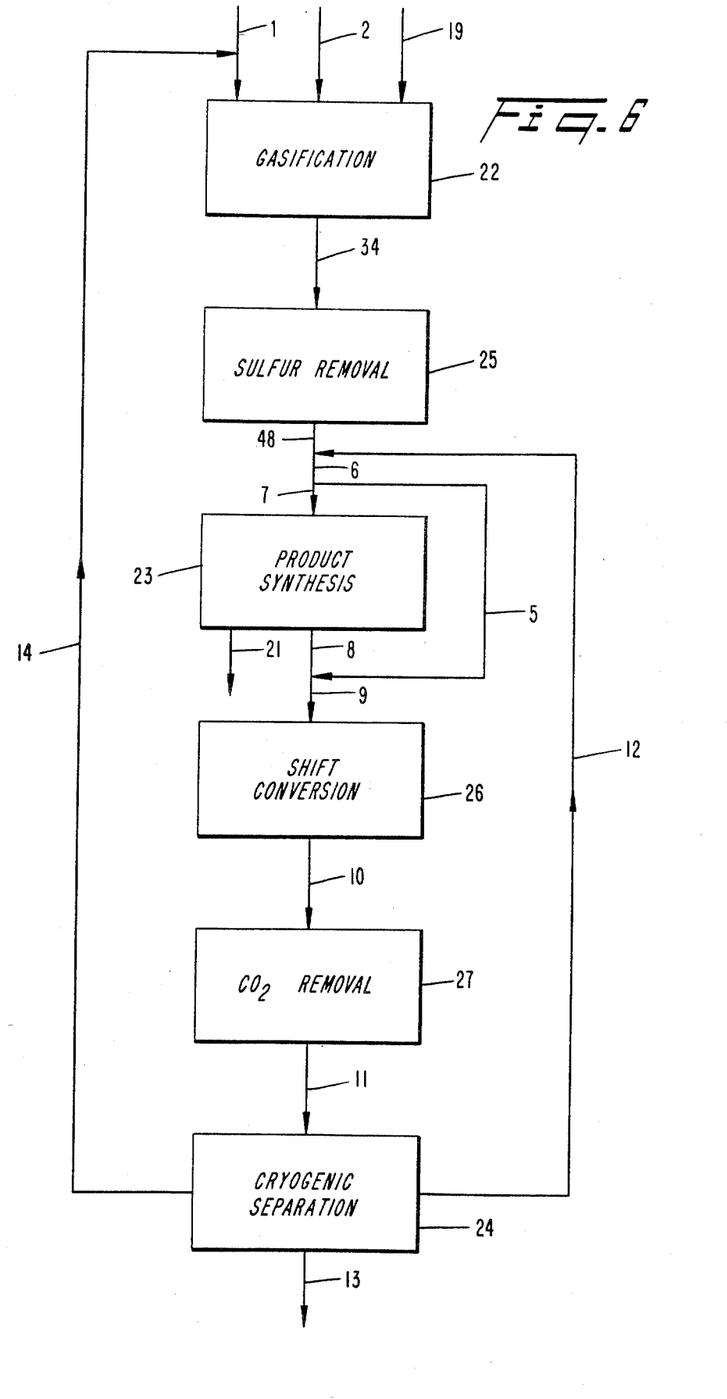
FIG. 6 is a block diagram showing a synthesis step bypass stream and optional steps for treatment of the combined purge gas stream/bypass stream.

FIG. 6 shows an embodiment of the invention which can eliminate the need for $CO_2$ removal prior to the synthesis step. In this embodiment, a portion of the synthesis gas stream bypasses the synthesis step via bypass stream 5. The bypass stream 5 is mixed with purge gas stream 8. The combined streams 9 are then subjected to shift conversion, $CO_2$ removal, and cryogenic separation. The shift conversion reactor preferably contains one or two beds of "low temperature" shift catalyst and operates in the range of 180° C. to 260° C. The gas leaving the shift conversion reactor has a CO content in the range of 0.1 to 1.0 mole percent on a dry basis, and preferably in the range of 0.3 to 0.6 percent.

In performing the process of the present invention, the choice between the various means of recycling the methane-rich stream to the process from the cryogenic separation step depends on several factors such as the size of the plant and the type of feedstock gasification process used.

If the gasification does not require a transport gas to supply the feedstock to the gasification reactor, and if the plant is of a large size, for example above 1000 MT/D of methanol, then it would be preferable to reform the methane-rich stream with steam and oxygen successively, as shown in FIG. 4. If the gasification process requires a transport gas, then the methane-rich stream may be used for that purpose, either as such, or after steam reforming. For small size plants, below 1000 MT/D methanol, the preferred embodiment would include recycling the methane-rich stream to the gasification reactor after reforming.

The processing schemes proposed or used for the production of many other oxygenated organic compounds are essentially the same as those for methanol. These processes have the same disadvantages as noted above for methanol synthesis. Accordingly, the present invention would acheive the same advantages in the production of such oxygenated organic compounds by the basic steps outlined above. Methanol is an example of the type of compounds that can be made, and a process for the production of methanol is a preferred embodiment.

Figure 7:
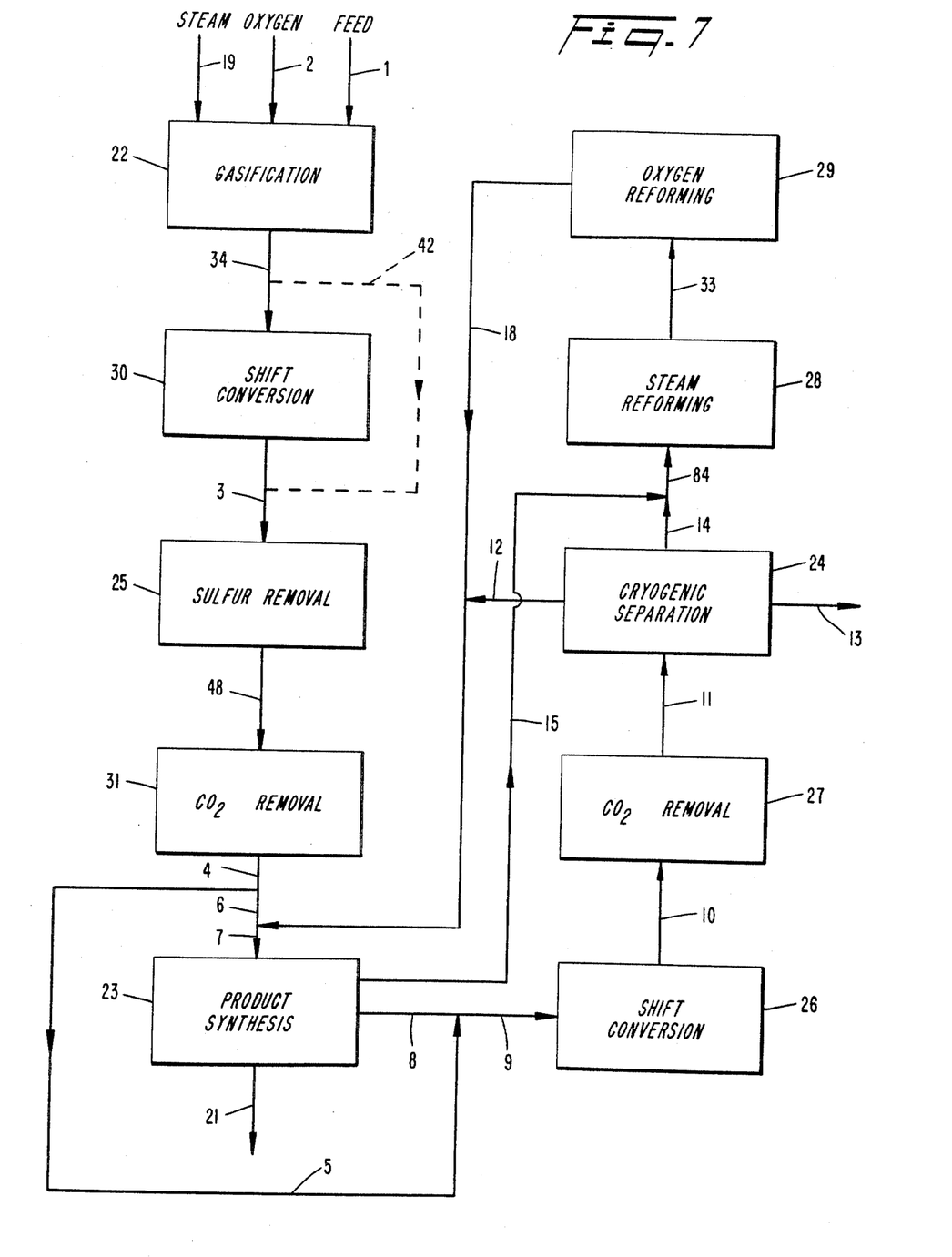
FIG. 7 is a block diagram incorporating various steps that may be used in the practice of the invention.
Figure 8C:
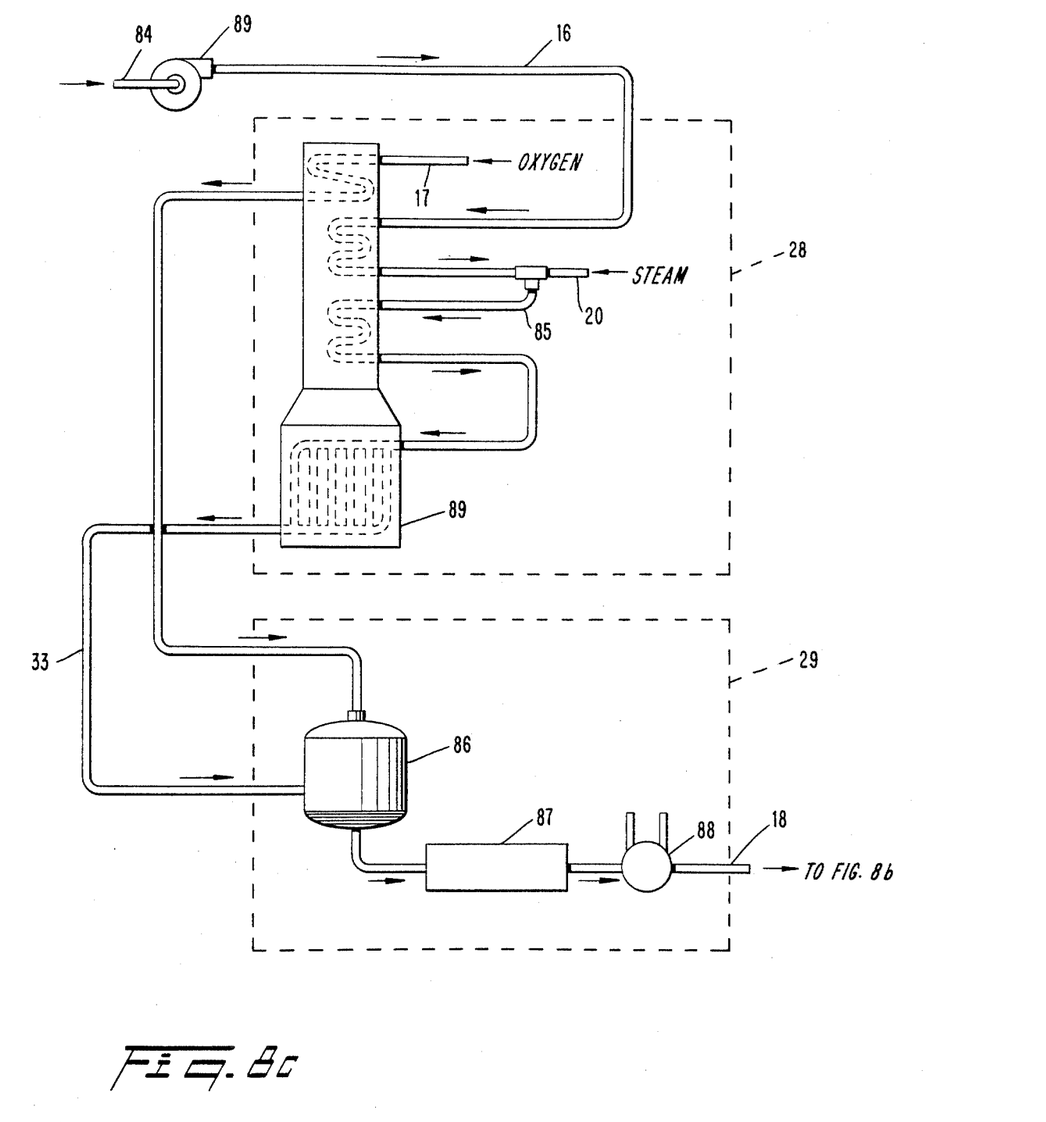

FIGS. 8A, 8B, and 8C show a detailed embodiment of the present invention. The dashed lines in the figures outline the basic process steps shown in FIG. 7.

The invention comprises the steps of gasification of a feedstock containing carbon. In FIG. 8A, the carbonaceous feedstock 1 is preferably coal. High purity oxygen 2 and steam 19 are added to the coal in a fluidized bed reactor 35. The pressure of this reactor is preferably above 20 atm, but preferably less than 100 atm. The temperature in the reactor is between 800° and 1250° C. Residual ash is removed from the effluent in a cyclone separator 36.

The gasification reactor may have catalyst particles in the fluidized bed. These particles are usually based on nickel and metals of the same family as active components. The chemical composition of appropriate catalyst components is known to those skilled in the art.

Gas stream 34, leaving cyclone separator 36, may be partially subjected to shift conversion 30. The fraction of gas stream 34 that is to be shift converted is quenched with water. Excess water is separated in drum 37. If necessary, additional steam is mixed with effluent stream 38. The effluent stream is then preheated in heat exchanger 39 before entering shift converter 40. The converter contains at least one bed of shift catalyst such as the HTS and MTS catalysts described above. The converter operates adiabatically with a temperature rise across the catalyst of about 50° C. to 100° C., depending on the CO content of the incoming gas. The effluent gas 41, which should have a CO content of about 1 to about 3 mole percent on a dry basis, is cooled in heat exchanger 39 and then mixed with the other fraction of the raw synthesis gas.

The fraction of raw synthesis gas stream 34 that is not subjected to shift conversion, bypass stream 42, is cooled in a waste heat boiler 43, and in heat exchanger 44. Bypass stream 42 is then washed with water in scrubber 45 before mixing with the shift converted gas stream 41 to form raw synthesis gas stream 3.

Raw synthesis gas stream 3 is then subjected to sulfur removal 25. Sulfur removal is accomplished by cooling raw synthesis gas stream 3 in a heat exchanger 46 and then scrubbing the sulfur compounds in a scrubber 47.

The purified raw synthesis gas 48 is sent to $CO_2$ removal 31. The solvent used in scrubber 47 is regenerated in a regeneration column 49.

Carbon dioxide is removed from at least a fraction of the purified raw synthesis gas stream 48 in scrubber 50. The solvent used in scrubber 50 is regenerated in a regenerator 51. The effluent gas from the $CO_2$ scrubber 50 is recombined with any gas that bypassed $CO_2$ removal to form a raw synthesis gas stream 4.

As shown in FIG. 8B, raw synthesis gas stream 4 is compressed in compressor 52 and is then split into a synthesis gas stream 6 and a bypass stream 5. Synthesis stream 6 is mixed with a hydrogen-rich recycle stream 12 (after the hydrogen-rich stream is compressed to a proper pressure for mixing) to form a final synthesis gas stream 7. The composition of stream 7 is preferably, but not necessarily, close to the stoichiometric composition for methanol synthesis. Stream 7 is injected into the synthesis loop 23.

As embodied in FIG. 8B, the synthesis loop 23 comprises two reactors, 61 and 62, arranged in series, a recycle stream 54, and a purge gas stream 8. More specifically, final synthesis gas stream 7 is mixed with recycle stream 54 and pressurized in a compressor 55, which raises the pressure of the feed gas to compensate for pressure loss through the loop. The temperature of the pressurized mixture is raised in heat exchanger 56. Feed mixture stream 57 is split into a direct feed stream 58 and a side feed stream 59. The direct feed stream 58 is heated in a heat exchanger 60 and fed into the first stage of the first reactor 61. Reactor 61 is arranged in 3 stages and side feed stream 59 is split between the second and third stages. The side feed acts as a source of fresh feed for the reactor and acts as a cooling fluid to lower the temperature of the reactants. A lower temperature favors the production of methanol. Reactors 61 and 62 are filled with a copper containing catalyst and are maintained at about 190° to about 290° C.

The effluent from the first reactor is cooled in heat exchanger 60 before insertion into the second reactor 62 which contains the same catalyst and operates at the approximately same temperature range as the first reactor. The effluent from the second reactor is successively cooled in heat exchangers 63, 56, and 64. The effluent stream at this point is preferably 4–8 mole percent methanol and is at a temperature of about 15° C. to about 50° C. Condensed raw methanol is separated in drum 65 and flashed to a lower pressure in drum 66. The liquid effluent from drum 66 is drawn off as crude methanol stream 21, and the gaseous overhead becomes flash stream 15.

The gaseous fraction from drum 65, stream 67, is split into recycle stream 54 and a purge gas stream 8. The amount of purge gas is selected so that the methane mole percent in the loop is maintained at less than 35 mole percent, perferably about 5 to about 35 mole percent, more perferably about 10 to about 20 mole percent methane. The mole percentage of methane in the loop will, of course, be the same percentage as in purge stream 8.

Purge gas stream 8 is mixed with bypass stream 5 to form purge stream 9. Purge stream 9 is injected with steam and sent to shift conversion 26.

As embodied in FIG. 8B, shift conversion 26 comprises the steps of preheating purge gas stream 9 in a heat exchanger 68 and then passing stream 15 through a shift conversion reactor 69 containing a low temperature shift catalyst. The effluent from the shift converter has a CO content of 0.1 to 1.0 mole percent on a dry basis, perferably 0.3 to 0.6 percent. Heat is recovered from the shift converted gas in exchanger 68 before the converted gas is sent to $CO_2$ removal 27.

As embodied in FIG. 8B, the step of $CO_2$ removal comprises cooling the shift converted gas in a heat exchanger 70 to form an input stream 10. Input stream 10 is scrubbed in a scrubber 71 and the solvent, which may be the same solvent as in sulfur removal, is regenerated in a regenerator 72. The effluent stream 73 from the $CO_2$ removal step is dried in a drum 74 that may contain molecular sieves.

It is possible to carry out the steps of $CO_2$ removal and water removal using two cryogenic exchangers 75 such as described below. Since ice and dry ice will form on the cryogenic exchanger 75 if no $CO_2$ removal and drying take place, one cryogenic exchanger is in operation while the other is being derimed.

The effluent dried gas stream 11, after $CO_2$ removal, is sent to cryogenic heat exchanger 75 and cooled. It emerges as partially condensed stream 76, and the liquid therein is separated in drum 77. The temperature in drum 77 is about $-130°$ to about $-180°$ C.

The gas fraction from drum 77 is hydrogen-rich stream 12. Stream 12 is used in cryogenic exchanger 75 to cool stream 11 and is then recycled to the methanol synthesis loop 23 by mixing with stream 6. The amount of argon in stream 12 is generally less than 15 percent of the total argon contained in stream 11, and preferably less than 10 percent.

The liquid fraction from drum 77, stream 78, is sent to cryogenic distillation column 79. At the top of column 79, maintained at about $-140°$ to about $-185°$ C., argon-rich stream 82 is drawn off, expanded through valve 83, to a pressure of about 6 atm and is used as a coolant in column 79. The argon-rich stream in then used to cool stream 11 in cryogenic exchanger 75 before becoming argon-rich stream 13. Stream 13 may be used as described above. Less than 6 percent of the total hydrogen in stream 11 is lost through stream 13.

At the bottom of column 79, maintained at a temperature of $-90°$ to $-150°$ C., conventional reboiling heat is added (not shown) and methane-rich stream 80 is drawn off. Methane-rich stream 80 is expanded through valve 81, and is used at the top of column 79 as a coolant for condensation. The stream is then used to cool the incoming stream 11 in cryogenic exchanger 75 and becomes methane-rich stream 14. Methane-rich stream 14 is mixed with flash stream 15 to form stream 84 which is further processed in FIG. 8C.

The step of steam reforming 28 is shown in FIG. 8C. Methane-rich stream 84 from FIG. 8B is compressed in compressor 89 to form methane-rich stream 16 and preheated in the convection section of a reformer 89. The preheated gas stream has steam 20 added to form stream 85. Stream 85 is preheated in the convection section of reformer 89 and then steam reformed in tubes as discussed above to form steam reformed stream 33.

As shown in FIG. 8C, steam reformed stream 33 is subjected to oxygen reforming in a secondary reformer 86. High purity oxygen 17 is used to reform stream 33, after the oxygen is preheated in the convection section of reformer 89. The effluent stream from secondary reformer 86 is cooled in waste heat boiler 87 and heat exchanger 88 to form recycle stream 18. Stream 18 is recycled and mixed with hydrogen-rich stream 12 as shown in FIG. 8B.

EXAMPLE

Table 1 shows an example of anticipated temperatures, gas pressure, flow rate, and composition at significant positions in a process according to FIGS. 8A, 8B, and 8C for the production of 2857.7 metric tons per day of methanol (as $CH_3OH$).

The stream numbers of Table 1 correspond to those of FIGS. 8A, 8B, and 8C. Stream 1 is a coal feedstock which has the following elemental composition (including 10% by weight of water):

| | | |
|---|---|---|
| carbon | 69.4% | by weight |
| hydrogen | 5.7% | by weight |
| oxygen | 8.9% | by weight |
| sulfur | 1.0% | by weight |
| ash | 15.0% | by weight |

Low heating value: 6000 kcal/kg.

In FIG. 8A, the gas stream 34 leaving the reactor 35 is at 1034° C. and 34.5 atm g. The gas is cooled in a waste heat boiler 43 and in two heat exchangers (one of which is not shown in FIG. 8A). The step of shift conversion 30 before synthesis 23 is not used in this hypothetical example. $CO_2$ removal 31 is also not done. The gas is then desulfurized by scrubbing in an absorber 47. In the absorber, the solvent used may be the dimethylether of polyethylene glycol (Selexol solvent).

The stream 48 leaving the sulfur absorber 47, since no $CO_2$ removal 31 is practiced, becomes stream 4 and is split as shown in FIG. 8B between bypass stream 5 going to shift conversion 26, and stream 6 going to the methanol synthesis loop 23. The synthesis is a low pressure synthesis, operating at about 60 atm, and using a copper based catalyst which is widely used commerically.

The shift converter is loaded with the so-called "low temperature" shift catalyst containing copper and zinc as active components. Purge stream 8 from the synthesis loop is mixed with bypass stream 5, to form stream 9 and stream 9 is shift converted in reactor 69. The mixture is subsequently scrubbed in absorber 71 to remove $CO_2$ using the same solvent as in the sulfur stripper 47 (shown in FIG. 8A). The mixture is then dried over molecular sieves in drum 74. Residual traces of carbon dioxide are also removed by the molecular seives.

The methane-rich stream 14 from the cryogenic exchanger 75 is first mixed with a flashed gas stream 15, and the mixture is compressed to 58 atm g, and is then steam reformed as shown in FIG. 8C using a steam/carbon ratio of 2.7. The outlet temperature of the reforming step is 754° C. After reacting with oxygen in the oxygen reformer 86, the temperature reached by the mixture at the outlet of the reactor is 957° C. The gas is then cooled in waste heat boiler 87 and in an exchanger 88 to form recycle stream 18. Stream 18 is recycled and mixed with hydrogen-rich stream 12.

TABLE 1

Figure 8Z:
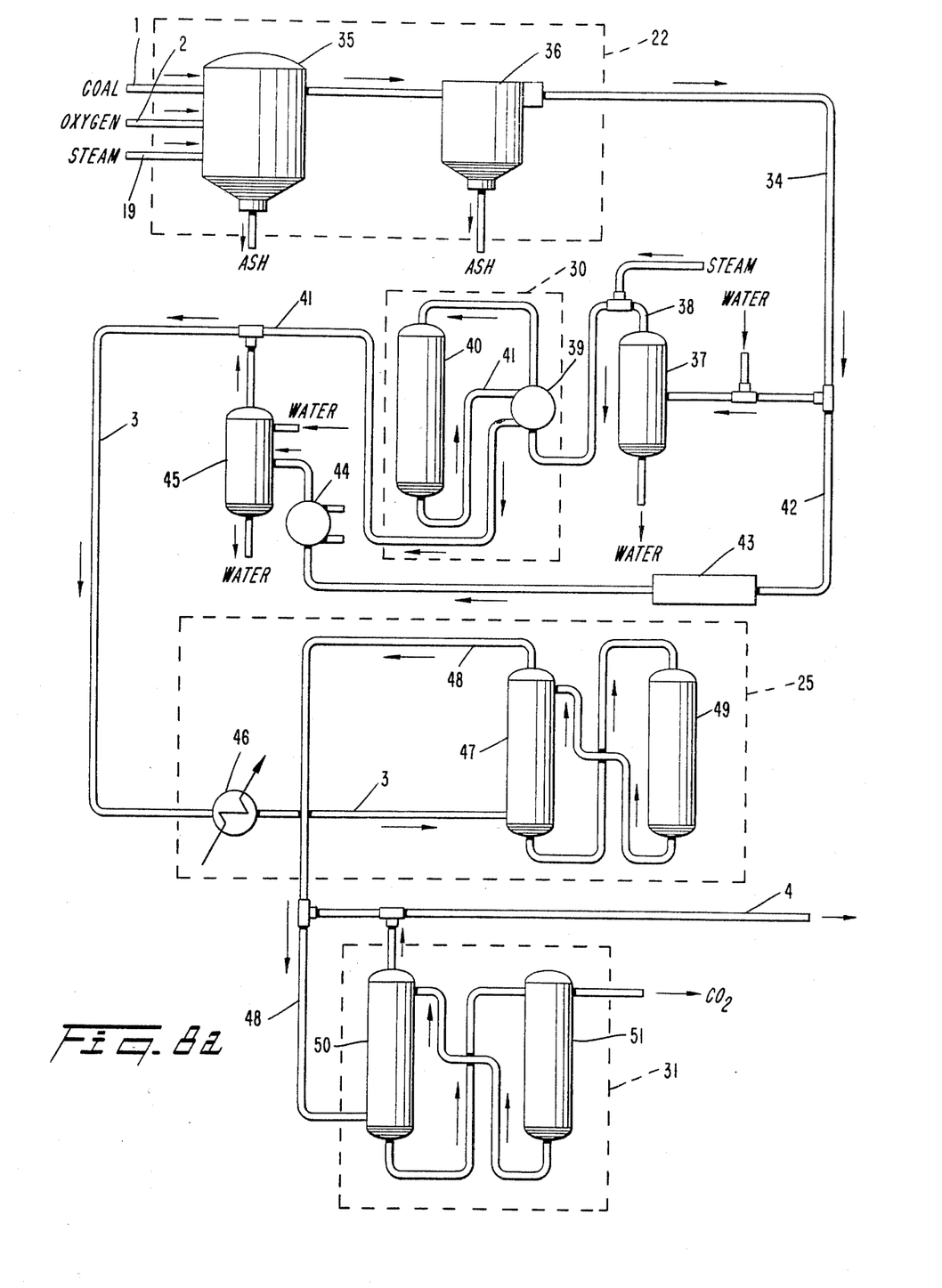

Temperature, pressure, composition and flow rate of process gas streams in FIG. 8.

| Stream number | 1* | 2 | 3 | 4 | 5 | 6 | 7 | 8 | 9 |
|---|---|---|---|---|---|---|---|---|---|
| $H_2$ KG MOL/HR | | 5060 | 5052 | 2273 | 2779 | 10900 | 2121 | 4394 | |
| CO | | | 4383 | 4369 | 1966 | 2403 | 2851 | 299 | 2265 |

TABLE 1-continued

Temperature, pressure, composition and flow rate of process gas streams in FIG. 8.

| | | | | | | | | | | |
|---|---|---|---|---|---|---|---|---|---|---|
| $CO_2$ | | | 3160 | 2723 | 1225 | 1498 | 1734 | 433 | 1658 | |
| $CH_4$ | | | 629 | 624 | 681 | 343 | 412 | 400 | 681 | |
| $A_r$ | | 19.2 | 19.2 | 19.2 | 8.6 | 10.6 | 21.8 | 21.2 | 29.8 | |
| $H_2S$ | | | 44 | | | | | | | |
| COS | | | 1.1 | | | | | | | |
| $O_2$ | | 3827 | | | | | | | | |
| $H_2O$ | | | 7150 | 4 | 1.8 | 2.2 | 6.1 | 0.7 | 2.5 | |
| TOTAL | | 3846.2 | 20446.3 | 12791.2 | 5755.4 | 7035.8 | 15924.9 | 3274.9 | 9030.3 | |
| TEMPERATURE °C. | 100 | 500 | 10 | 30 | 30 | 30 | 38 | 38 | 38 | |
| PRESSURE atm g | 38 | 39 | 34.0 | 33.7 | 57.1 | 57.1 | 57.1 | 57.1 | 57.1 | |

| Stream number | 10 | 11 | 12 | 13 | 14 | 15 | 16 | 17 | 18 | 19 | 20 |
|---|---|---|---|---|---|---|---|---|---|---|---|
| $H_2$ KG MOL/HR | 6603 | 6537 | 6513 | 24 | 0 | 24 | 24 | | 1608 | | |
| CO | 56 | 56 | 29 | 27 | 0 | 4 | | | 419 | | |
| $CO_2$ | 3867 | 0 | 0 | 0 | 0 | 44 | 44 | | 236 | | |
| $CH_4$ | 681 | 647 | 22 | 8 | 644 | 10 | 654 | | 47 | | |
| $A_r$ | 29.8 | 29.8 | 7.0 | 20.1 | 2.7 | 0.4 | 3.1 | 1.1 | 4.2 | | |
| $H_2S$ | | | | | | | | | | | |
| COS | | | | | | | | | | | |
| $O_2$ | | | | | | | | | 222 | | |
| $H_2O$ | 6.8 | | | | | 0.6 | 0.6 | | 3.9 | 9390 | 1762 |
| TOTAL | 11243.6 | 7296.8 | 6571 | 79 | 646.7 | 83.0 | 729.7 | 223.1 | 2318.1 | 9390 | 1762 |
| TEMPERATURE °C. | 25 | 25 | 20 | 20 | 20 | 38 | 38 | 150 | 38 | 500 | 500 |
| PRESSURE atm g | 56.3 | 55.8 | 53.8 | 0.5 | 0.5 | 3.7 | 58.8 | 55.8 | 53.8 | 39 | 58.8 |

*Total coal feedstock is 145,805 kg/h containing (weight %): C: 69.4%; H: 5.7%; O: 8.9%; S: 1.0%; ash: 15.0%

It will be apparent to those skilled in the art that various modifications and variations could be made in the process of the invention without departing from the scope or spirit of the invention.

What is claimed is:

1. A process for the production of an oxygenated organic product from a feedstock containing carbon, comprising the steps of:
   (a) gasifying said feedstock by reacting said feedstock adiabatically with an oxygen-rich gas stream, at a temperature between 800° C. and 1250° C. to produce a raw synthesis gas having a methane content between 1 and 10 mole percent on a dry basis;
   (b) mixing said raw synthesis gas stream with a hydrogen-rich gas stream to form a final synthesis gas stream;
   (c) injecting said final synthesis gas into a synthesis loop, forming said oxygenated organic product in said loop, and extracting from said loop a purge gas stream in an amount to maintain between about 5 and about 35 mole percent methane circulating in the synthesis loop;
   (d) separating said purge gas stream cryogenically to form a hydrogen-rich gas stream, an argon-rich gas stream, and a methane-rich gas stream; and
   (e) recycling said hydrogen-rich gas stream to step (b).

2. The process of claim 1, further comprising the step of recycling at least part of said methane-rich gas stream by mixing with said feedstock.

3. The process of claim 1, further comprising the steps of reforming at least part of said methane-rich gas stream and then mixing with said hydrogen-rich gas stream and said synthesis gas stream.

4. The process of claim 1, wherein said oxygenated organic product is methanol.

5. The process of claims 1, 2, 3, or 4, further comprising the steps of:
   (a) removing substantially all sulfur compounds from said raw synthesis gas before mixing said raw synthesis gas with said hydrogen-rich stream; and
   (b) removing essentially all carbon dioxide contained in said purge gas stream.

6. The process of claims 1, 2, 3, or 4, further comprising the steps of:
   (a) gasifying said feedstock by reacting said feedstock adiabatically with an oxygen-rich gas stream, at a temperature between 800° C. and 1250° C. to produce a raw synthesis gas having a methane content between 1 and 10 mole percent on a dry basis;
   (b) removing substantially all sulfur compounds from said raw synthesis gas to form a purified synthesis gas;
   (c) mixing said purified raw synthesis gas with said hydrogen-rich stream to produce a final synthesis gas; and
   (d) removing essentially all carbon dioxide from said purge gas stream.

7. The process of claim 1, 2, 3, or 4, further comprising the steps of:
   (a) removing substantially all sulfur compounds from said raw synthesis gas before mixing said raw synthesis gas with said hydrogen-rich stream;
   (b) subjecting said purge gas stream to a shift conversion reaction; and
   (c) removing substantially all carbon dioxide from said shift converted purge gas stream.

8. The process of claim 6, further comprising the steps of:
   (a) subjecting said purge gas stream to a shift conversion reaction prior to removing the carbon dioxide from said purge gas; and
   (b) subjecting at least part of said methane-rich stream to a steam reforming reaction by reacting said methane-rich stream with steam over a reforming catalyst in externally heated tubes, at a temperature between 600 and 1,000° C.

9. The process of claim 3, or 4, further comprising the step of combining said feedstock with said methane-rich stream.

10. A process for producing an oxygenated organic product from a feedstock containing carbon comprising the steps of:
    (a) combining said feedstock with a methane-rich stream to form a mixture;

(b) gasifying said mixture by reacting said mixture with an oxygen-rich gas stream at a temperature between 800° C. and 1,250° C. to produce a raw synthesis gas having a methane content between 1 and 10 mole percent on a dry basis;
(c) removing essentially all the sulfur compounds from said raw synthesis gas stream to form a purified synthesis gas stream;
(d) mixing said purified synthesis gas stream with a hydrogen-rich stream to form a final synthesis gas;
(e) injecting said final synthesis gas into a synthesis loop, producing said oxygenated organic product, and extracting from said loop a purge gas stream in an amount to maintain between about 5 and about 35 mole percent methane circulating in the synthesis loop;
(f) subjecting said purge gas stream to a shift conversion reaction by reacting said purge gas stream with steam over a shift catalyst;
(g) removing essentially all the $CO_2$ from the purge gas stream after the purge gas has been subjected to shift conversion;
(h) separating said substantially $CO_2$ free purge gas stream cryogenically into a hydrogen-rich stream, an argon-rich stream, and a methane-rich stream;
(i) recycling said hydrogen-rich stream to step (d); and
(j) recycling at least part of said methane-rich stream to step (a) above.

11. The process of claim 10, wherein part of said purified synthesis gas, after sulfur removal, is mixed with said purge gas and the mixture is subjected to shift conversion, $CO_2$ removal, and cryogenic separation.

12. The process of claim 1, 2, 3, 4, 10, or 11, wherein essentially all the energy required for refrigeration for the cryogenic separation step is supplied by expansion of at least one effluent stream from said cryogenic separation.

13. The process of claim 1, 2, 3, 4, 10 or 11, further comprising the step of subjecting at least part of said raw synthesis gas stream to a shift conversion reaction, by reacting said raw synthesis gas stream with steam in the presence of a shift catalyst to convert essentially all carbon monoxide in said raw synthesis gas stream to carbon dioxide and hydrogen.

14. The process of claim 14, further comprising the step of removing an appreciable fraction of carbon dioxide contained in said raw synthesis gas stream after said raw synthesis gas stream has been subjected to shift conversion.

15. The process of claim 1, 2, 3, 4, 10, or 11, wherein said raw synthesis gas comprises 2 to 6 mole percent methane on a dry basis.

16. The process of claim 2, 3, 10, or 11, wherein said oxygenated organic product is methanol.

17. The process of claim 1, 2, 3, 4, 10, or 11, wherein all processing steps are carried at essentially the same pressure level.

18. The process of claim 1, 2, 3, 4, 10, or 11, wherein the processing steps from gasification to mixing are carried out at a pressure of 20 to 60 atm and the synthesis step is carried out at a pressure of 50 to 100 atm.

19. The process of claim 1, 2, 3, 4, 10, or 11, wherein gasification is carried out in a fluid bed reactor.

20. The process of claim 19, wherein gasification is carried out in the presence of a catalyst.

21. The process of claim 1, 2, 3, 4, 10, or 11, wherein said final synthesis gas has the stoichiometric composition required for methanol synthesis.

22. The process of claim 1, 2, 3, 4, or 10 wherein the step of gasifying includes reacting said feedstock adiabatically with an oxygen-rich gas stream at a temperature between 950° C. and 1,100° C.

23. The process of claim 1, 2, 3, or 4, wherein said purge synthesis loop contains between 10 and 20 mole percent methane.

24. A process for the production of methanol from a feedstock containing carbon, comprising the steps of:
(a) gasifying said feedstock by reacting said feedstock adiabatically with an oxygen-rich gas stream, at a temperature between 800° C. and 1250° C. to produce a raw synthesis gas having a methane content between 1 and 10 mole percent on a dry basis;
(b) mixing said raw synthesis gas stream with a hydrogen-rich gas stream to form a final synthesis gas stream;
(c) injecting said final synthesis gas into a synthesis loop, forming said methanol in said loop, and extracting from said loop a purge gas stream in an amount to maintain between about 5 and about 35 mole percent methane circulating in the synthesis loop;
(d) separating said purge gas stream cryogenically to form a hydrogen-rich gas stream, an argon-rich gas stream and a methane-rich gas stream; and
(e) recycling said hydrogen-rich gas stream to step (b).

* * * * *